United States Patent [19]

Austin et al.

[11] Patent Number: 4,824,969

[45] Date of Patent: * Apr. 25, 1989

[54] PROCESS FOR PREPARING CYCLIC CARBONATE ESTERS FROM OLEFINS IN A SINGLE REACTION MIXTURE

[75] Inventors: Richard G. Austin, Ridgewood; Robert C. Michaelson, Kinnelon; Richard S. Myers, Fairlawn, all of N.J.

[73] Assignee: Exxon Research & Engineering Co., Florham Park, N.J.

[*] Notice: The portion of the term of this patent subsequent to Jan. 29, 2002 has been disclaimed.

[21] Appl. No.: 685,713

[22] Filed: Dec. 24, 1984

[51] Int. Cl.$^4$ .................. C07D 317/26; C07D 319/06
[52] U.S. Cl. .................................... 549/230; 549/229; 568/860
[58] Field of Search ................. 549/229, 230; 568/860

[56] References Cited

U.S. PATENT DOCUMENTS

| | | | |
|---|---|---|---|
| 2,397,630 | 4/1946 | Strain | 549/230 |
| 2,873,291 | 2/1959 | Spiegler | 549/230 |
| 3,025,305 | 3/1962 | Verdol | 549/230 |
| 3,153,051 | 10/1964 | Kormendy et al. | 549/230 |
| 4,009,183 | 2/1977 | Fumagalli et al. | 549/230 |
| 4,028,423 | 6/1977 | Brownstein et al. | 568/910 |
| 4,224,223 | 9/1980 | Wheaton et al. | 549/230 |
| 4,247,465 | 1/1981 | Kao et al. | 549/230 |
| 4,496,778 | 1/1985 | Myers et al. | 568/860 |
| 4,496,779 | 1/1985 | Myers et al. | 568/860 |

FOREIGN PATENT DOCUMENTS 71286 2/1983 European Pat. Off.
1303756 1/1973 United Kingdom.

OTHER PUBLICATIONS

M. Schroeder, Chemical Reviews (1980) vol. 80, pp. 187–213.

Primary Examiner—Robert T. Bond
Attorney, Agent, or Firm—S. H. Markowitz; T. B. Morris

[57] ABSTRACT

A process for reacting in admixture, an olefin with oxygen, CO, and water, to form a cyclic alkylene carbonate, in the presence of a catalyst composition comprising a catalytically active osmium compound, copper containing co-catalyst I (e.g. $CuBr_2$) and a co-catalyst II (e.g. pyridine) is disclosed.

17 Claims, No Drawings

PROCESS FOR PREPARING CYCLIC CARBONATE ESTERS FROM OLEFINS IN A SINGLE REACTION MIXTURE

BACKGROUND OF THE INVENTION

The present invention relates to a process for converting olefins directly to cyclic alkylene carbonate esters in a single step in the presence of a gaseous mixture of carbon monoxide and a molecular oxygen containing gas.

Cyclic carbonate esters resembling cyclic esters of vicinal glycols are well known in the art. They are useful as solvents for polymers and for selective extraction procedures. They are also intermediates for preparing epoxides, glycols, ethanolamines, polyesters and other glycol esters. Because of the ability of cyclic alkylene carbonates to react with the evolution of carbon dioxide, they may also find use as blowing agents for preparing foamed plastic or elastomeric compositions.

The more common methods for preparing cyclic alkylene carbonate esters can be classified broadly according to the starting reactants employed, namely, alkylene oxides, vicinal chlorohydrins, or olefins.

Representative of the alkylene oxide route is U.S. Pat. No. 2,773,881 which reacts an epoxide with carbon dioxide, employs a nitrogen-base catalyst such as an amine, e.g. primary, secondary and preferably tertiary amines (trimethylamine, piperidine), in conjunction with pressures of $CO_2$ above 500 psi and tempratures of 100° to 400° C.

Other catalysts suitable for use in the alkylene oxide routine as described in the background of U.S. Pat. No. 4,224,223 include quarternary ammonium halides, quarternary ammonium hydroxides, sodium bicarbonate, ion-exchange resins, bis-(aminoethoxy) tin compounds, and polyhalogenated 5- or 6-membered ring hydrocarbons.

Representative of the halohydrin route are U.S. Pat. Nos. 2,784,201; 3,923,842; 4,226,778; and 4,231,937.

More specifically, U.S. Pat. No. 2,784,201 is directed to a process for making ethylene carbonate wherein sodium alkyl carbonate is reacted with ethylene chlorohydrin to form the alkyl hydroxyalkyl carbonate which in turn undergoes an internal ester exchange to form the ethylene carbonate. No catalyst is employed and the reaction is conducted at atmospheric pressure.

U.S. Pat. No. 3,923,842 is directed to a process wherein a vicinal halohydrin is reacted with carbon dioxide, in a solvent and in the presence of an amine catalyst compound, i.e., primary, secondary or tertiary amines, e.g. triethylamine. The vicinal halohydrin can be prepared by reacting an olefin with oxygen in the presence of an iron halide and a copper halide producing ferric oxide as a co-product. At Col. 3, Lines 27 et seq, a three step process for the production of an oxirane compound is disclosed wherein an olefin is converted to a halohydrin; the halohydrin converted to the cyclic carbonate ester with $CO_2$ and an amine; and the cyclic carbonate ester decomposed to the oxirane compound and $CO_2$. The production of the halohydrin from an olefin and subsequent conversion to the cyclic carbonate ester in a single reaction mixture is not disclosed.

U.S. Pat. No. 4,226,778 is directed to a process for synthesizing cyclic alkylene carbonate esters wherein a vicinal halohydrin is reacted with a quarternary: ammonium, phosphonium, arsonium or stibonium-bicarbonate, in the presence of $CO_2$ and an organic diluent. Elevated $CO_2$ pressures are preferred.

U.S. Pat. No. 4,231,937 is directed to a process for synthesizing cyclic alkylene carbonate esters, wherein an alkylene iodohydrin is reacted with $CO_2$ in the presence of molecular oxygen and a catalyst mixture comprising (1) an iodide of the metals of Groups IA, IB, IIA, IIb and VIII of the Periodic Table, and (2) a carbonate of the metals of Groups IB, IIA, and IIB of the Periodic table, at a pH of between 3 and 10. Included within the scope of metal iodides are cuprous iodides, and osmium iodides. The iodohydrin can be prepared as described in U.S. Pat. No. 3,923,842 discussed above, i.e. from an olefin. However, the in-situ preparation of the iodohydrin in the presence of $CO_2$ and oxygen is not disclosed.

Representative of the olefin route are U.S. Pat. Nos. 3,025,305; 4,009,183; 4,224,223; 4,247,465; and 4,325,874.

U.S. Pat. No. 3,025,305 discloses a dual catalyst system to effect formation of the cyclic carbonate ester by the direct oxidation of olefins in the liquid phase with a carbon dioxide and oxygen mixture. The first catalyst component (Catalyst A) is a salt or other compound of a transition metal of atomic numbers 23 to 29, as well as lead and tungsten. Specific metals disclosed are vanadium, chromium, manganese, iron, cobalt, nickel, and copper. Halide salts are the preferred form of Catalyst A. The second catalyst component (Catalyst B) is the halide or hydroxy form of a quarternary ammonium compound.

U.S. Pat. No. 4,009,183 discloses a process for preparing cyclic carbonate esters by reaction, in the liquid phase, between an olefin, carbon dioxide, and oxygen in the presence of a catalyst system consisting of (a) iodine in the form of elementary iodine and the iodides of Groups IA, IIA, IB, IIB, IIIA, IIIB, IVA, VA, VIIB and VIII of the Periodic Table; and (b) an oxygen conveyor selected from manganese dioxide, nitrites, nitrates, nitrogen oxides and a cobalt complex. Preferred iodides include copper iodide. Water, or water solvent mixtures (e.g. 10:1 to 1:10) can be employed. The pH of the reaction mixture is maintained between 3 and 8.

U.S. Pat. No. 4,244,223 is directed to the synthesis of cyclic carbonate esters in the liquid phase by reacting an olefin, and carbon dioxide in the presence of oxygen and using a dual catalyst mixture of (a) iodine or an iodate of a metal of Groups IA, IB, IIA, IIB, VB, VIIB, and VIII of the periodic Table; and (b) an iron compound, copper compound or mixture thereof deposited on an inert support. Osmium is not specifically disclosed as a suitable metal. Cuprous iodide is a suitable iodine containing compound. The supported copper compound includes cuprous or cupric halides. Water or a mixture of water and water miscible solvents can be employed including N,N-dimethylformamide and sulfolane.

U.S. Pat. No. 4,247,465 contains a related disclosure of U.S. Pat. No. 4,224,223, but in the absence of a support.

U.S. Pat. No. 4,325,874 employs a catalyst system similar to U.S. Pat. No. 4,224,223 with the exception that the iron and copper compound of the 2nd catalyst component is replaced with an oxide or weak acid salt of thallium III or gold III.

It will be noted that all of the above discussed patents employ carbon dioxide as a source of the carbonyl group of the cyclic carbonate ester. Furthermore, when the cyclic carbonate ester is prepared from an olefin using CO$_2$, water is not produced as a co-product.

In contrast, the halohydrin route produces water which can lead to hydrolysis of the carbonate ester, and to problems in separating the resultant glycol from the ester.

It is also known to produce non-cyclic carbonate esters from monohydric alcohols by reacting two of such alcohols with carbon monoxide and oxygen as described in Br. Patent Specification No. 1,303,756. More specifically, the process of this patent employs a catalyst composition which is a complex of a compound of a metal of Groups IB, IIB, or VIII of the Periodic Table. The specific metals illustrated are Cu, Ag, Au, Zn, Cd, Hg, Fe, Co, and Ni. The catalyst complex made from the metals of the above metal compounds, comprises a ligand, which complexes with said metal, selected from organic bases such as pyridine, dipyridyl, phenanthroline, alkyl or aryl phosphines, dimethylsulfoxide, dimethylformamide, quinuclidine, CO, nitriles, malonitrile, succinonitrile, and adiponitrile. The positive charge of the metal/ligand complex is associated with a halide ion. A complex formed from Cu$_2$Cl$_2$ and pyridine is illustrated in Example 1. The deficiencies of this catalyst system are discussed in European patent application (EPA) Pub. No. 71,286, namely, sensitivity to water co-product in the form of reduced selectivity and reaction rate.

The above deficiencies are alleged to be overcome in EPA Pub. No. 71,286 by employing a sulfone in conjunction with a copper compound. The copper may be in the I or II valent state, but preferably a copper II compound is employed. Complexes of copper as identified in Br. Patent Specification No. 1,303,756 containing anions and neutral ligands either preformed or made in-situ can be employed. The preferred catalyst system is a copper I and II halide in conjunction with a tertiary aliphatic amine such as trimethylamine. The alcohol reactant may contain one or more hydroxyl groups. However, it is stated that when the alcohol contains 2 or more of such hydroxyl groups, the resulting carbonate is generally polymeric. Glycols are not specifically illustrated as a suitable alcohol. An inert solvent can be employed in addition to the sulfone. The presence of water in the form of impurities in reaction components (e.g. associated with the sulfolane) is said to be tolerated in the process although it is preferred to remove the water and separate it from the carbonate by azeotropic distillation. The organic amine bases are employed to achieve a molar ratio of base to copper of 0.01 to 1.

By way of further background, it is well known from the technical literature, that olefins can be oxidized to their corresponding diols, stoichiometrically or catalytically with osmium oxide compounds, particularly osmium tetroxide.

The non-catalytic, i.e. stoichiometric, cis-hydroxylation of alkenes with OsO$_4$ has been conventionally characterized as taking place via the formation, with the alkene, of an osmium (VI) intermediate ester complex. [For a recent review, see, "Osmium Tetroxide Cis Hydroxylation of Unsaturated Substrates", by M. Schroder, Chem. Rev. Vol. 80, pp. 187-213 (1980) hereinafter Schroder].

To convert the non-catalytically prepared osmium (VI) ester complex intermediate to the diol, the intermediate can be hydrolyzed reductively. Reductive hydrolysis is conventionally carried out by using alkali metal sulfites, bisulfites, lithium aluminum hydride, or hydrogen sulfide to yield the corresponding cis-diols together with lower valence forms of osmium which are removed by filtration.

It has been observed by Criegee (See, Schroder, page 191, Col. 1, 11-12) that for non-catalytic cis hydroxylation of alkenes, the rate of formation of the Osmium (VI) ester complex is greatly increased in the presence of tertiary amines such as pyridine. This rate enhancement is believed to occur via the formation of some type of amine Osmium (VI) ester complex (See Schroder page 191, Col. 2). However, enhancement of the rate of the Osmium (VI) ester complex does not necessarily result in an enhancement of the overall hydroxylation rate, since the rate of hydrolysis of the ester complex must also be considered. In this regard, it has been noted that whereas certain osmium ester complexes and amine ester complexes (e.g. with pyridine) can be hydrolyzed reductively, amine ester complexes are more resistant to such hydrolysis. (See Schroder page 191, Col. 2, last paragraph; and page 193, Col. 1, first paragraph).

In contrast to the stoichiometric non-catalytic mode of cis hydroxylation with OsO$_4$, the catalytic mode employs a secondary oxidant to oxidatively hydrolyzed the intermediate Osmium (VI) ester and regenerate the OSO$_4$ which can undergo further reduction by the substrate olefin. A variety of oxidants have been employed in conjunction with OsO$_4$ such as H$_2$O$_2$, t-butylhydroperoxide and oxygen.

The use of oxygen as an oxidant has encountered considerable difficulty due to the appreciable overoxidation of the products, particularly at elevated temperatures (e.g. 70°-80° C.), leading to the formation of keto or acid products. However, if the reaction temperature is lowered to reduce overoxidation, the reaction rate is so low that yields of cis-diol are drastically reduced. An additional disadvantage of the use of oxygen oxidan is that the reaction is highly pH dependent (See Schroder, page 210, Col. 1).

Commonly assigned U.S. Pat. No. 4,390,739 by R. Austin, and R. Michaelson describes a process for the hydroxylation of olefins using oxygen as an oxidant, a catalytically active metal oxide catalyst such as OsO$_4$, and at least one transition metal salt co-catalyst such as copper bromide. This process can also be conducted in the optional presence of a second co-catalyst such as alkali metal halides. Pyridine is disclosed as a suitable solvent for this process but no mention is made of any promoting effect being associated with this solvent medium. While the use of the transition metal co-catalyst substantially improves the reaction rate and/or selectivity of the hydroxylation reaction, a further improvement in this process is still being sought.

U.S. patent application Ser. No. 310,217, filed Oct. 9, 1981, now abandoned, of common assignee herein by R. Michaelson and R. Austin discloses the use of various osmium halide and oxyhalide catalysts in the presence or absence of a wide variety of co-catalysts and an oxidant selected from hydrogen peroxide, organohydroperoxides, or oxygen. Pyridine is disclosed as a suitable buffer for pH control in this application, which pH control is required when employing hydrogen peroxide.

Commonly assigned U.S. Pat. No. 4,314,088 and a continuation-in-part thereof, namely, U.S. Pat. No. 4,393,253 by R. Austin and R. Michaelson collectively, disclose the use of various halide containing co-catalysts in conjunction with osmium tetroxide catalyst and organohydroperoxide oxidants to hydroxylate olefins. The halide containing co-catalysts include alkali and alkaline earth metal halides, hydrogenhalides, quarternary hydrocarbyl phosphonium halides, halogens, and transition metal halides.

Commonly assigned U.S. Pat. No. 4,413,151, by R. Michaelson, R. Austin, and D. White is directed to a process for hydroxylating olefins in the presence of a supported osmium containing catalyst, optional cocatalyst (e.g. $CuBr_2$) and an oxidant selected from hydrogen peroxide, organohydroperoxides and oxygen.

Commonly assigned U.S. patent application Ser. No. 420,137 filed Sept. 20, 1982 by R. Michaelson, R. Austin, and D. White, now U.S. Pat. No. 4,486,613, is directed to a process for hydroxylating olefins in the presence of an osmium carbonyl catalyst optional cocatalysts and an oxidant selected from hydrogen peroxide, organohydroperoxide, and oxygen.

While all of the above described commonly assigned patents or patent applications disclose the use of pyridine as one of many suitable solvents, none of these applications show or suggest either alone or collectively, that any promoting effect can be obtained from pyridine when employed for the hydroxylation of olefins, or in accordance with the presently claimed invention.

Moreover, to the best of the inventors' knowledge, not a single prior art publication shows the use of any tertiary amine as a promoter to enhance the overall rate of osmium catalyzed cis-hydroxylation of olefins with oxygen. The catalytic cis hydroxylation of tetra and tri-substituted alkenes with t-butylhydroperoxide and $OsO_4$ has apparently been conducted. However, the oxidative hydrolysis of such esters has been found to be particularly slow due to steric considerations and particularly in the presence of pyridine (See, Schroder, page 193, Col. 2, first paragraph).

Commonly assigned U.S. patent application Ser. No. 538,190, filed Oct. 3, 1983 by the inventors herein is directed to the use for olefin hydroxylation of heteroaromatic and pseudoheteroaromatic amine promoters, such as pyridine, in a reaction system employing a catalytically active osmium compound, a copper compound (e.g. copper bromide) and oxygen.

Commonly assigned U.S. patent application Ser. No. 604,043, filed Apr. 26, 1984 by the inventors herein is directed to the use of olefin hydroxylation of cycloaliphatic amine based promoters such as DABCO (defined hereinafter) and hexamethylenetetramine in a reaction system similar to that described in connection with the U.S. patent application No. 538,190.

The search has continued for alternative methods for producing cyclic carbonate esters. The present invention is a result of this search.

SUMMARY OF THE INVENTION

The present invention is directed to a process wherein cyclic alkylene carbonate esters can be prepared directly from olefins, i.e., in a single reaction mixture or zone, in the presence of carbon monoxide and oxygen. It has been discovered that by controlling reaction conditions, the water co-product produced by carbonylation of aglycol with CO can be effectively utilized as a source of water, believed to function as a co-reactant in the conversion of olefins to glycols.

While the exact mechanism is not understood, and without wishing to be bound by any particular theory, the process of the present invention can be viewed as occuring in two stages. In the first stage, an olefin is converted to a glycol intermediate, in the presence of CO, and a catalyst composition comprising an osmium catalyst, a copper co-catalyst I, and a particular amine co-catalyst II by reaction with water and oxygen. In this stage water is consumed in the reaction. In the second stage, in the presence of the same catalyst composition, the glycol intermediate reacts with the CO and oxygen present in the reaction mixture to form water and the corresponding cyclic alkylene carbonate ester.

Whereas water is consumed in the first stage of reaction, it is produced in the second reaction stage. Accordingly, by carefully controlling catalyst composition in conjunction with the total amount of water in the reaction mixture, a delicate balance can be established wherein the detrimental effects of water on the second reaction stage can be obviated, or at least reduced substantially, by simultaneously employing this water as a reactant in the first stage of reaction. Both the first and second reaction stages are therefore conducted in a single reaction zone which contains all the necessary components for both reactions to occur.

Accordingly in one aspect of the present invention there is provided a process for preparing at least one cyclic alkylene carbonate ester which comprises reacting in a liquid phase admixture at least one olefin containing at least one ethylenic unsaturation, water, molecular oxygen, and carbon monoxide, in the presence of a catalyst composition, in a manner and under conditions sufficient to result in the addition of a carbonyldioxy group across at least one of said olefinic ethylenic unsaturation thereby forming said cyclic alkylene carbonate ester product, with the proviso that the total amount of water present in said liquid phase during reaction is maintained in a manner sufficient to provide a molar ratio of water to ethylenic unsaturation to be reacted of from about 0.1:1 to about 20:1; said catalyst composition comprising:

(A) at least one catalytically active osmium containing compound;

(B) at least one copper containing compound co-catalyst I having an identity and in an amount effective to increase at least one of the rate and selectivity in the formation of said cyclic carbonate ester product relative to its absence;

(C) at least one co-catalyst II having an identity and in an amount effective to increase the rate of said cyclic carbonate ester product formation relative to its absence, said co-catalyst II being selected from at least one member of the group consisting of:

(i) 1,4-diazabicyclo[2.2.2]octane;
(ii) hexamethylenetetraamine; and
(iii) at least one compound represented by at least one of the structural formulae:

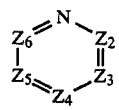

(XIIIa)

or

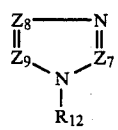

(XIIb)

wherein:

(1) in structural formula (XIIa):

(a) $Z_2$ to $Z_6$ independently represent a member selected from the group consisting of a methylidyne group, a substituted methylidyne group represented by the formula $\equiv CR_{11}$, and a tertiary nitrogen group; said $R_{11}$ substituent being selected from the group consisting of hydroxy, alkyl, aryl, aralkyl, and alkaryl; and (b) any two of said $R_{11}$ substituents located on adjacent carbons of said $Z_2$ to $Z_5$ groups of structural formula (XIIa) together can constitute part of a monocyclic or fused bicyclic ring system, which partial ring systems are (i) aromatic, or heteroaromatic in nature, said heteroatom being nitrogen, and (ii) completed by, and fused with parent structure (XIIa) through said adjacent carbons to $Z_2$ to $Z_5$ groups; and (2) in structural formula (XIIb)

(a) $Z_7$ to $Z_9$ independently represent a member selected from the group consisting of a methylidyne group, and a substituted methylidyne group represented by the formula $\equiv CR'_{11}$ wherein $R'_{11}$ is independently selected from the group consisting of alkyl, aryl, aralkyl, and alkaryl; and (b) $R_{12}$ is selected from the group consisting of alkyl, aryl, aralkyl, and alkaryl.

DESCRIPTION OF PREFERRED EMBODIMENTS

In accordance with the present invention an olefin, water, molecular oxygen and carbon monoxide are reacted in the liquid phase in the presence of a catalyst composition in a manner sufficient to result in the addition of a carbonyldioxy group (i.e.

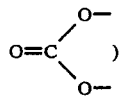

)

across the ethylenic unsaturation of the olefin as illustrated by the folllowing sequence:

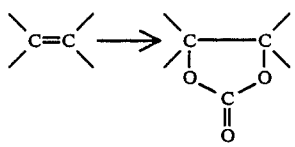

Eq. 1

In the above sequence, the carbonyl group is derived from the carbon monoxide, while the dioxy groups are believed to be derived from the oxygen and water reactants and formed by the oxidative carbonylation of a vicinal diol intermediate not shown. The vicinal diol intermediate is believed to result from the hydroxylation of the olefin.

I. Olefin

Olefins which can be converted in accordance with the present invention contain at least one ethylenic unsaturation and comprise any of the unsaturated aliphatic or alicyclic compounds well known in the art for undergoing such hydroxylation reactions. Typically, such compounds will contain from 2 to about 20 carbons, preferably from 2 to about 10 carbons, and most preferably from 2 to about 5 carbons. Such compounds may be straight branched chain or cyclic, mono-olefinic, di-olefinic or polyolefinic, conjugated or non-conjugated. They may be substituted with such groups as alkenyl, e.g., $C_1$ to $C_{10}$ alkenyl, aralkenyl, e.g., $C_8$ to $C_{14}$ aralkenyl, aryl, e.g., $C_6$ to $C_{14}$ aryl, alkyl, e.g., $C_1$ to $C_{10}$ alkyl, or aralkyl and alkaryl wherein the alkyl and aryl portions thereof are as described above, as well as with functional groups such as hydroxyl, carbonyl and anhydride.

Typical of such olefins are those represented by the structural formula:

(I)

wherein $R_1$, $R_2$, $R_3$, and $R_4$, which may be the same or different, are selected from the group consisting of hydrogen; substituted or unsubstituted: alkenyl, aralkenyl, alkyl, aryl, alkaryl, and aralkyl hydrocarbyl groups, said hydrocarbyl groups being preferably as defined immediately above; or any two or said $R_{1-4}$ groups together can constitute a cycloalkyl group typically of from about 4 to about 12, preferably from about 5 to about 8 carbons.

Most preferably, the olefin contains from about 2 to 6 carbon atoms and contains a terminal carbon-to-carbon double bond, i.e. an alpha-olefin.

Representative olefins which can be converted and contain at least one ethylenic saturation include: ethylene, propylene, butene-1, butene-2, isobutene, pentene-1, pentene-2, hexene, isohexene, heptene, 3-methylhexene, octene-1, isooctene, nonene, decene, dodecene, tridecene, pentadecene, octadecene, eicosene, docosene, tricosene, tetracosene, pentacosene, butadiene, pentadiene, hexadiene, octadiene, decadiene, tridecadiene, eicosadiene, tetracosadiene, cyclopentene, cyclohexene, cycloheptene, methylcyclohexene, isopropylcyclohexene, butylcyclohexene, octylcyclohexene, isopropylcyclohexene, butylcyclohexene, octylcyclohexene, dodecylclohexene, acrolein, acrylic acid, 1,2,3,4-tetrahydrophthalic anhydride, allyl alcohol, methyl methacrylate, styrene, cholestrol, and the like.

The preferred olefins are ethylene, propylene, butenes, pentenes, hexenes, cyclohexenes, styrene, allyl alcohol and allyl chloride.

The most preferred olefins are propylene, ethylene, and butenes.

II. Osmium Compound (Catalyst)

In accordance with the present invention, the oxidative state of osmium in osmium catalyst as initially added to the reaction mixture is not critical to catalytic activity when the appropriate co-catalyst system is employed as described hereinafter, i.e., any osmium compound as described herein when subjected to reaction conditions as described herein, itself possesses, or is converted under such reaction conditions to a species which possesses, at least the capability of catalyzing the reaction, e.g., hydroxylation of olefins with oxygen.

In view of the above, it is possible to flexibly tailor the identity of the osmium compound and co-catalyst system described herein to achieve an extremely efficient catalyst system for forming the hydroxylated intermediate from olefins with oxygen. In selecting the particular osmium compound for use in the present invention, the volatility and/or toxicity of the comppound, and its activity in the system employed will be taken into consideration.

More specifically, included within the scope of the osmium compound (the term "osmium compound" is defined herein broadly to also include ionic and neutral complexes of osmium and a ligand) which can be employed in the process of the present invention include in their order of preference halogenated osmium compounds, ionic osmium compounds, osmium oxides, osmium oxides, osmium complexes, osmium carbonyls, and osmium metal.

Osmium-halogen containing comppounds include osmium halides and osmium oxy halides, and complexes thereof, (all of the above being referred to herein collectively as osmium-halides) such as those represented by the structural formulae: $Os(X)_n$ (e.g., $OsX_3$, $OsX_4$, and $OsX_5$); $Os(OH)X_3$; $OsOX_4$; $OsO_3X_2$; $OsONX_4$; $(M)_{n'}[OsX_6]^{-2}$; $(M)_{n'}[OsO_2X_4]^{-2}$; $M^{+1}[Os(OH)X_5]^{-1}$; $(M)_{n'}[OsO_4X_2]^{-2}$; $(M)_{n'}[OsO_2(OH)_2X_2]^{-2}$; $(M)_{n'}[OsNX_5]^{-2}$; and mixtures thereof: wherein X is halogen independently selected from the group consisting of F, Cl, Br, and I; n is an integer which can vary from 1 to 6 (e.g. 3 to 5), M is a cation including cations of alkali metals, (e.g. Li, Na, K, Rb, Cs, Fr), alkaline earth metals (e.g., Be, Mg, Ca, Sr, Ba, Ra), ammonium (i.e., $NH_4^+$), tetrahydrocarbyl ammonium (e.g. $(R)_4N^+$) and tetrahydrocarbyl phosphonium (e.g. $(R)_4P^+$) said tetrahydrocarbyl groups being typically $C_1$ to $C_5$ alkyl; and n' is a number which is selected in conjunction with the valence of cation M to achieve neutral complex; preferably n' is 1.

Representative examples of such compounds include $OsF_3$, $OsCl_3$, $OsBr_3$, $OsI_3$, $OsF_4$, $OsCl_4$, $OsBr_4$, $OsI_4$, $OsF_5$, $Os(OH)Cl_3$, $Os(OH)F_3$, $OsOF_4$, $OsOCl_4$, $OsO_3F_2$, $OsONCl_4$, $K_2[OsCl_2Br_2I_2]$, $(NH_4)_2[OsF_6]$, $Ca[OsI_6]$, $Li_2[OsO_2Cl_4]$, $(CH_3CH_2)_4N[Os(OH)Cl_5]$, $Mg[OsO_4F_2]$, $Na_2[OsO_2(OH)_2Cl_2]$, $Ba[OsNCl_5]$, $K_2[OsNCl_5]$, $(CH_3CH_2)_4P[Os(OH)Br_5]$, $Mg[OsNBr_5]$, $Na_2[OsO_2(OH)_2Br_2]$, $Ba[OsNCl_5]$, $K_2[OsNCl_5]$, $K_2[OsNCl_5]$, $K_2[OsNBr_5]$, and mixtures thereof.

The preferred compounds of this class are those having a boiling point at atmospheric pressure of typically greater than about 130° C., preferably greater than about 150° C., and most preferably greater than about 175° C.

The most preferred compounds are those represented by the structural formula $OsX_3$ such as $OsBr_3$.

In selecting the appropriate halogen for the osmium-halide the order of preference in terms of activity is Br, Cl, I and F.

The compounds having the formula $Os(X)_n$ can be prepared by the general methods described in "Advanced Inorganic Chemistry" by Cotton and Wilkinson (hereinafter Cotton and Wilkinson), p. 909 (4th ed. 1980).

Compounds having the formula $OsOX_4$ and $OsO_3X_2$ can be prepared by the method described in the "J. Inorganic Nuclear Cchemistry" by Hepworth and Robinson, Vol. 4, p. 24 (1957).

Compounds having the formula $Os(OH)X_3$ can be prepared by the method described in "Comprehensive Inorganic Chemistry", Trotman-Dickenson (ed.) Vol. 3, p. 1217 (1973).

Compounds having the formula $OsONX_4$ can be prepared by the method described in "Comprehensive Inorganic Chemistry" described above at Vol. 3, p. 1233.

Compounds having the formula $(M)_{n'}[OsX_6]^{-2}$ can be prepared by the general method described in Cotton and Wilkinson, p. 919.

Compounds having the formula $(M)_{n'}[OsO_2X_4]^{-2}$ can be prepared by the general method described in Cotton and Wilkinson, p. 917.

Compounds having the formula $M^{+1}[Os(OH)X_5]^{-1}$ can be prepared by the general method described in "Z. Anorg. Allgen. Chem" by Krauss and Wilken (hereinafter Krauss and Wilken) Vol. 137, p. 349 (1924).

Compounds having the formula $(M)_{n'}[OsO_4X_2]^{-2}$ can be prepared by the method described in Krauss and Wilken, Vol. 145, p. 151 (1925).

Compounds having the formula $(M)_{n'}[OsO_2(OH)_2X_2]^{-2}$ can be prepared by the method described in Cotton and Wilkinson, p. 914.

Compounds having the formula $(M)_{n'}[OsNX_5]^{-2}$ can be prepared by the method described in "Inorganic Synthesis", by E. G. Rochow, Vol. 6, p. 204 (1960).

The disclosures of all of the above references illustrating the methods of preparation of the aforenoted osmium-halide compounds are herein incorporated by reference.

The term osmium carbonyl compound is defined herein broadly to also include, in addition to compounds, ionic and neutral complexes of osmium with at least one carbonyl ligand and optionally other ligands such as phosphines, hydride, halide and the like as described hereinafter.

Thus, suitable osmium carbonyl compounds include $Os(CO)_5$, $Os_2(CO)_9$, $Os_3(CO)_{12}$, $Os_5(CO)_{16}$, $Os_6(CO)_{18}$, $Os_7(CO)_{21}$, and $Os_8(CO)_{23}$.

Osmium carbonyl complexes suitable for use as the osmium carbonyl catalyst include those represented by the formulae: $[Os(CO)X'_5]^{-2}$, $[Os(CO)_2X'_4]^{-2}$, $[Os(CO)_3X'_3]^{-1}$, $[Os(CO)_4X']^{-2}$, and $Os(X'')_a(CO)_b(Y)_c(PR'_3)_d$, wherein X' is halogen, preferably bromine, X'' is independently selected from hydrogen (i.e. hydride), cyclopentadienyl (CDP), and halogen (preferably bromine), Y is independently selected from NO, $NH_3$, and $N_2$, R' is a hydrocarbyl group independently selected from alkyl, typically alkyl of from about 1 to 10, preferably from about 1 to 5, most preferably from about 1 to 3 carbons, aryl, typically aryl of from about 6 to about 14, preferably from about 6 to about 10, most preferably about 6 carbons, alkaryl and aralkyl wherein the alkyl and aryl groups thereof are as defined immediately above, "a" and "c" represent numbers of from 0 to about 3, "b" represents a number of at least 1, "d" represents a number of 2 or 3 and the sum of a, b, c, and d is selected in conjunction with the valence of Os to achieve a neutral complex.

Representative examples of suitable osmium carbonyl complexes include $[Os(CO)Cl_5]^{-2}$, $[Os(CO)I_5]^{-2}$, $[Os(CO)_2Br_4]^{-2}$, $[Os(CO)_2I_4]^{-2}$, $[Os(CO)_3I_3]^{-2}$, $[Os(CO)_3I_3]^{-1}$, $[Os(CO)_3Cl_3]^{-1}$, $[Os(CO)_4I]^{-2}$, $[Os(CO)_4Cl]^{-2}$, $Os[(\pi-CPD)_2(CO)P\phi_3]_2$, $OsCl_2(CO)(P\phi_3)_2$, $Os(CO)_3(P\phi_3)_2$, $OsHCl(CO)$ $(P\phi_3, OsI(CO)(NO)(P\phi_3)_2$, $OsHCl(CO)$ $(PEt_2\phi)_3$, $OsI_2(CO)(P\phi_3)_2$, $OsHI(CO)(P\phi_3)_3$, and mixtures thereof; "Et" representing ethyl, "$\phi$" representing phenyl, and $\pi$—CPD representing pi-bonded cyclopentadienyl.

The preferred osmium carbonyl compound is $Os_3(CO)_{12}$.

The aforenoted osmium carbonyl compounds can be prepared by conventional methods as described in "Inorganic Synthesis", Vol. 13, p. 92 (F. A. Cotton ed. 1972); "Quarterly Reviews", Vol. 24, p. 498 (1970); and "Advanced Inorganic Chemistry", Cotton and Wilkinson, p. 1000 to 1017 (3rd. ed. 1972).

Representative osmium oxides include $OsO_2$, $OsO_3$, $OsO_4$, and mixtures thereof. The preferred osmium oxide is $OsO_4$.

Representative ionic osmium oxide compounds can be represented by the formula:

 (II)

wherein M' is a cation of an alkali or alkaline earth metal, ammonium, or tetraalkyl ammonium, preferably tetraalkyl ammonium in which the alkyl group has from about 1 to about 5 carbons, and x and y are numbers such that 2y-x is the valence of the osmium in any compound defined by this formula. While the preferred ionic osmium compounds of this class are the perosmates ($M'_2OsO_5$) other ionic osmium compounds such as $M'_2OsO_4$ (known as osmates), $M'_2OsO_3$, and $M'OsO_2$ can also be employed.

Representative of osmium complexes include those which form with ligands of $PR'_3$ (R' being as described above), amines, nitride, $\pi$-bonded cyclopentadienyl ($\pi$—CPD), and mixtures thereof.

Illustrative osmium phosphine complexes can be represented by the structural formula:

 (III)

wherein X" is independently selected from hydrogen (e.g., hydrido) cyclopentadienyl (CPD), and halogen (preferably bromine); Y is independently selected from NO, $NH_3$, and $N_2$; R' is hydrocarbyl group independently selected from alkyl, typically alkyl of from about 1 to about 10, preferably from about 1 to 5, most preferably from about 1 to 3 carbons, aryl, typically aryl of from about 6 to about 14, preferably from about 6 to about 10, most preferably about 6 carbons, alkaryl and aralkyl wherein the alkyl and aryl groups thereof are as defined immediately above, "d" and "e" are numbers of from 0 to about 3, "f" is a number of 2 to 4 (e.g. 2 to 3) and the sum of d, e, and f is selected in conjunction with the valence of Os to achieve a neutral complex.

Representative examples of suitable osmium phosphine complexes include $OsH_2(N_2)(P\phi_3)_3$; $OsH_2(P\phi_3)_4$; $OsCl_2(P\phi_3)_3$; $OsCl_3(NO)(P\phi_3)_2$; $OsCl(NO)(P\phi_3)_2$; $OsCl_2(NH_3)(PEt_2\phi)_3$; $Os[(\pi—CPD)_2(NH_3)(P\phi_3)]_2$; and mixtures thereof; "Et" representing ethyl, "$\phi$" representing phenyl, and $\pi$—CPD representing pi-bonded cyclopentadienyl.

Illustrative osmium amine complexes include aromatic amine complexes illustrated by $[Os(bipy)_3]^{+2}$ wherein bipy is 2,2'-bipyridine, and $[Os(NH_3)_5]^{+2}$ wherein X is halogen, preferably Br.

Illustrative osmium nitride complexes include $[OsO_3N]^-$; $K[OsO_3N]$; and $OsO_3NC(CH_3)_3$.

Illustrative $\pi$—CPD complexes include $Os(\pi—CPD)_2$.

Methods for preparing the aforedescribed osmium complexes are conventional and are summarized in Cotton and Wilkinson "Advanced Inorganic Chemistry", pages 1000-1017 (3rd ed. 1972).

The osmium containing compounds are employed in amounts effective to catalyze the formation of the vicinal diol intermediate, i.e. olefin hydroxylation. Thus while any effective amount of osmium catalyst will suffice, it is contemplated that such effective amounts constitute a ratio of the moles of osmium in the osmium compound to moles of ethylenic unsaturation to be hydroxylated in contact with said osmium compound of typically from about $1\times10^{-1}:1$ to about $1\times10^{-10}:1$, preferably from about $1\times10^{-2}:1$ to about $1\times10^{-6}:1$, and preferably from about $1\times10^{-2}:1$ to about $1\times10^{-5}:1$ Alternatively, such amounts may be expressed as varying from about 1 to about 10,000, preferably from about 10 to about 5,000, and most preferably from about 50 to about 1,000 ppm, based on the total weight of olefin and any other additives, solvent, or co-catalysts.

(III) Co-catalyst System

(A) Co-catalyst I

Co-catalyst I is a term used to refer to at least one organic or inorganic transition metal, i.e., copper, containing compound including complexes. Such copper compound will typically be initially employed as a salt having an anion and a cation, wherein the anion of said salt includes halide, pseudo halide, carboxylate, aryloate, and aryolate and other anions described hereinafter.

The cation transition metal of said co-catalyst I salts is copper.

More specifically, the anion of co-catalyst I includes:

(a) halide ions, in their order of preference as follows: bromide, chloride, iodide, fluoride;

(b) carboxylate anions, typically carboxylate anions represented by the structural formula:

 (IIIa)

wherein $R_5$ is selected from the group consisting of substituted and unsubstituted: alkyl, typically about $C_1$ to about $C_{10}$ alkyl, preferably about $C_1$ to about $C_5$ alkyl, and most preferably about $C_1$ to about $C_3$ alkyl; cycloalkyl, typically about $C_4$ to $C_{20}$ cycloalkyl, preferably about $C_5$ to $C_{15}$ cycloalkyl, and most preferably about $C_6$ to $C_{10}$ cycloalkyl; and aralkyl, typically aralkyl wherein the aryl group thereof is as defined in connection with Ar of structural formula IV below and the alkyl group thereof is as defined immediately above; said $R_5$ substituents including hydroxyl; halide (i.e., F, Cl, Br, and I); ether groups, typically ether groups represented by the structural formulae —O—$R_6$, and —R-7—O—$R_6$ wherein $R_6$ and $R_7$ are independently selected from the group consisting of alkyl, typically about $C_1$ to about $C_{10}$ alkyl, preferably about $C_1$ to about $C_5$ alkyl and most preferably about $C_1$ to about $C_3$ alkyl; and ester groups, typically ester groups, represented by the structural formulae

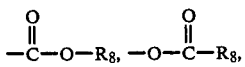

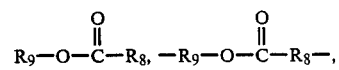

wherein $R_8$ and $R_9$ which may be the same or different are as defined in connection with $R_6$ and $R_7$;

(c) aryloate anions, typically aryloate anions represented by the structural formula:

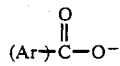
(IV)

wherein Ar is selected from the group consisting of substituted and unsubstituted: aryl, typically $C_6$ to about $C_{14}$ aryl, preferably $C_6$ to about $C_{10}$ aryl (e.g., $C_6$ aryl) and alkaryl, typically alkaryl wherein the alkyl group is as defined above in connection with $R_5$ being alkyl, and the aryl group thereof is as defined above, and wherein said substituents on the Ar group are as defined above in connection with $R_5$;

(d) aryolate anions, typically aryolate anions represented by the structural formula:
wherein Ar is as described above in connection with structural formula IV, and preferably is aryl; and (e) pseudo halide anions, defined herein to be selected from the group consisting of SCN—, CN—, SeCN—, TeCN—, OCN—, and CNO—; and

(V)

(f) anions selected from the group consisting of $NO_3$—, $R_{10}S$—, HS—, $R_{10}Se$—, HSe—, HTe—, and $R_{10}Te$—, $R_{10}$— being alkyl typically about $C_1$ to about $C_{10}$ alkyl, preferably $C_1$ to $C_5$ alkyl.

In short, the co-catalyst I, when employed as a salt, can be a single salt, or a mixture of salts and said salts can comprise copper and any of the aforenoted group (a)-(f) anions.

Representative examples of co-catalyst I salts include $CuF_2$, $CuBr_2$, $CuI_2$, $CuCl_2$, CuI, CuCl, CuBr, CuF, copper acetate, copper naphthoate, copper benzoate, copper propanoate, copper nitrate, copper 4-ethyl benzoate, copper 4-butyl benzoate, copper decanoate, copper hexanoate, copper phthalocyanine, copper 2-(methoxymethyl) acetate, copper 3-(ethoxy)propanoate, copper 4-(propoxy carbonyl)-butanoate, copper 3-(propyl carbonyl oxy)propanoate, copper 2-(methyl carbonyloxy methyl)acetate, copper 4-(ethoxy carbonyl methyl)butanoate, copper 4-(ethoxy methyl)benzoate, copper 3-(propoxy) naphthoate, copper 4-(ethoxy carbonyl)benzoate, copper 2-(hyroxy)acetate, copper 2-chloro propanoate, copper 4-(bromo) benzoate, copper 4-(hydroxy) benzoate, copper phenolate, copper naphtholate, copper 4-chloro phenolate, copper 5-(hydroxy) naphtholate, $Cu(CN)_2$, $Cu(SeCN)_2$, $Cu(TeCN)_2$, $Cu(OCN)_2$, $Cu(CH_3S)_2$, $Cu(CH_3CH_2S)_2$, $Cu(HS)_2$, $Cu(CH_3—CH_2—CH_2—Se)_2$, $Cu(HSe)_3$, $Cu(HTe)_2$, $Cu(CH_3Te)_2$, and mixtures thereof.

The preferred co-catalyst I salts include copper: bromide, chloride, iodide, nitrate and acetate.

The copper containing co-catalyst I is believed to function to not only enhance the rate and/or selectivity of the vicinal diol intermediate formation but also catalyzes the formation of the cyclic carbonate ester. If the amount of copper co-catalyst I is selected to maximize the vicinal diol intermediate formation, however, the yield of cyclic carbonate ester suffers significantly. Accordingly, it has been found that more copper co-catalyst I is desired for the two step reaction, than would otherwise be indicated when performing only an olefin hydroxylation reaction by itself. Accordingly, the amount of co-catalyst I is functionally related in the present invention to enhancing the rate and/or selectivity of the cyclic carbonate ester end product. However, because of the participation of osmium in the first stage of reaction, this amount can be related to the amount of osmium catalyst in the reaction mixture. Thus it is contemplated that effective amounts of the copper co-catalyst I constitutes a mole ratio of osmium to co-catalyst I in the reaction system in contact with the olefin, of typically from about 1:1 to about 1:1000, preferably from about 1:1 to about 1:500, and most preferably from about 1:1 to about 1:50.

(B) Co-catalyst II

Co-catalyst II is a tertiary nitrogen containing compound which also falls within the classification of cycloaliphatic amine (referred to herein as co-catalyst IIa), heteroaromatic amine (referred to herein as co-catalyst IIb), or pseudoheteroaromatic amine (referred to herein as co-catalyst IIc). Co-catalyst II must perform a dual function in the reaction system, namely, it must enhance the rate of formation of the vicinal diol intermediate from the olefin while simultaneously catalyzing, or assist in catalyzing (e.g. enhance the rate and/or selectivity) the formation of the cyclic carbonate ester. Failure to perform either of these two functions results in a significant drop in the cyclic carbonate ester yield. Furthermore the mere possession of a tertiary nitrogen does not qualify an amine as being suitable for the above dual functions. For example, it has been found that trialkylamines such as triethylamine actually supresses the overall rate of reaction as well as the rate of formation of the vicinal diol intermediate.

There are two cycloaliphatic amines which have been found suitable for the use as co-catalyst IIa, namely, 1,4-diazabicyclo[2.2.2]octane (referred to herein as DABCO) represented by the structural formula:

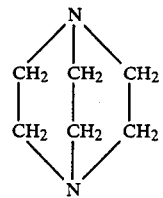
(VI)

and 2,3,5,7-tetraazatricyclo[3.3.1.1]decane also known as hexamethylenetetramine (HMTA) and represented by the structural formula:

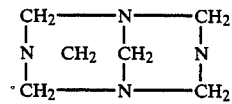
(VII)

and mixtures thereof.

The heteroaromatic and pseudoheteroaromatic amines suitable for use as co-catalysts II(b) and (c) are characterized by: (1) the possession of at least one tertiary nitrogen; (2) a heteroaromatic or pseudoheteroaromatic ring structure; (3) the absence of primary or secondary nitrogens in the aforenoted ring structures; (4) appropriate steric configuration of any substituents located on the aforenoted ring structures; (5) the absence of nitrogen atoms, in fused bicyclic or tricyclic heteroaromatic ring structures, having a configuration within said ring structures sufficient to enable a bidentate ligand relationship to exist with the copper of co-catalyst I; and (6) the absence of a 1,3- or 1,4- positional configuration between any two tertiary nitrogens present in said co-catalysts II(b) ring structures.

A heteroaromatic ring system or nucleus is defined herein to be one in which at least one carbon atom that is a member of an aromatic ring of an aromatic compound is replaced with a heteroatom (i.e. nitrogen) and the resulting compound contains the maximum number of conjugated double bonds compatible with the valency restrictions imposed by the heteroatom.

A pseudoheteromatic ring structure or nucleus is defined herein to be a 5 carbon membered ring system wherein at least one of the carbons present therein is replaced with a heteroatom (i.e. nitrogen) and the resulting compound contains the maximum number of conjugated double bonds compatible with the valency restrictions imposed by the heteroatom.

Co-catalysts II(b) and (c) are conveniently described with reference to pyridine for purposes of illustrating the tertiary nitrogen and steric requirements. For example, pyridine can be represented by the following structural formula:

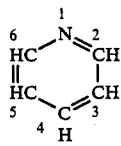

(VIII)

Pyridine performs as an excellent rate promoter of, for the reaction system described herein. It is believed that one of the essential features of the pyridine molecule responsible for the observed promoting effect is a tertiary amine nitrogen group located within and forming a part of an aromatic nucleus. However, it has also been found, that as the hydrogens located at the 2 and 6 positions of the pyridine ring are successively replaced with more bulky substituents, e.g. a methyl group, the promoting effect relative to pyridine is decreased due, it is believed, to steric hinderance about the tertiary nitrogen atom. Thus, it is believed that steric freedom about at least one of tertiary nitrogens of co-catalysts II(b) and (c) is an important consideration in selecting the identity of such co-catalysts.

The requirement of the absence of a primary or secondary nitrogen is best illustrated with reference to imidazole represented by the following structural formula:

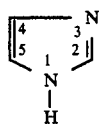

(IX)

Imidazole is not an effective rate promoter due, it is believed, to the presence of a secondary nitrogen at the number 1 position in the ring. When this nitrogen is converted to a tertiary nitrogen by substitution of a methyl group for the replaceable hydrogen, however, rate enhancement is imparted to the compound. The disadvantageous consequences of the presence of a secondary or primary nitrogen is not entirely understood, but it is believed that such nitrogens may be too basic, impart too great an ability to the co-catalysts II(b) and (c) to coordinate with the copper of co-catalyst I to the extent that it effectively prevents the copper from performing its intended function, and/or is too readily oxidized in-situ under reaction conditions.

Regarding the limitations of heteroaromatic fused bicyclic or tricyclic ring structures of co-catalyst IIb, it has been found that 4,5-diazaphenanthrene and 1,8-diazanaphthalene are not effective rate promoters. Both of these compounds possess two tertiary nitrogens in a fused bicyclic and tricyclic heteroaromatic ring system, respectively as follows:

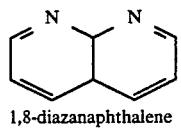

1,8-diazanaphthalene (X)

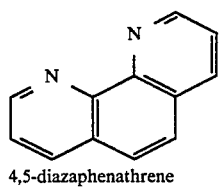

4,5-diazaphenathrene (XI)

The particular location of the two nitrogens is believed to be such that each nitrogen pair is capable of collectively interacting with the copper of co-catalyst I as a bidentate ligand, the 1,8-diazanaphthalene configuration permitting the formation of a 4 member ring with a central copper ion, and the 4,5-diazaphenanthrene permitting the formation of a 5 membered ring with a central copper ion. The functioning of the co-catalyst IIb as a bidentate ligand is believed to sufficiently disrupt the interaction of the copper with other components in the reaction mixture, that the rate enhancement is lost. Thus, it is believed that while co-catalyst IIb must possess the ability, to complex to some extent, (e.g. as a monodentate ligand) with the copper of co-catalyst I, the stability of the complex should not be so great (e.g. as in bidentate ligands) that the transition metal is, in practical effect, removed from interaction with the remainder of the components of the reaction mixture. Note that for fused tricyclic heteroaromatic ring systems, it is not considered possible for such compounds to act as tridendate ligands, although, if possible, such an occurrence would also sought to be avoided. In accordance with the above theory, and under the replacement nomemclature system of carbocyclic systems described in "Nomenclature of Organic Compounds" ed. Fletcher, J., Dermer, O., Fox, R., Advances in Chemistry Series 126, pp. 49 et seq. (1974), 1,8-diazanaphthalene, and their derivatives are considered ineffective co-catalysts.

Regarding the limitation relating to the relationship between any two tertiary nitrogens present in the ring structure of co-catalyst IIb, it has been found that in the series of diazabenzene isomers, only 1,2-diazabenzene is an effective, albiet slightly effective, rate promoter while 1,4- and 1,3-diazabenzenes actually inhibit reaction. The reason for this occurrence is not entirely understood, but has led to the conclusion that such 1,4- and 1,3-relationships between tertiary nitrogens present in a mono-, bi- or tri-cyclic fused heteroaromatic ring system should be avoided. Thus, for example, typically in a bi-cyclic ring system a maximum of 3, preferably 2, most preferably 1, tertiary nitrogen(s) will be present therein. Unsuitable diazanaphthalenes include 1,3-, 1,4-isomers thereof.

In view of the above functional requirements, suitable co-catalysts II(b) and (c) for use in the present invention can be represented by at least one of the structural formulae:

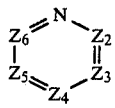
(XIIa)

and

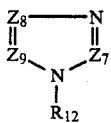
(XIIb)

wherein in structural formula (XIIa): $Z_2$ to $Z_6$ represent, independently, a methylidyne group (—CH=), a substituted methylidyne group (=CR$_{11}$), or a tertiary nitrogen group (—N=), all within a heteroaromatic nucleus containing nitrogen as the heteroatom therein. The substituent $R_{11}$ of $Z_2$ to $Z_6$ is selected from the group consisting of hydroxy; alkyl, typically about $C_1$ to $C_{10}$ alkyl, preferably about $C_1$ to $C_5$ alkyl, and most preferably about $C_1$ to $C_3$ alkyl; aryl, typically about $C_6$ to $C_{14}$ aryl, preferably $C_6$ to $C_{10}$ aryl, and most preferably $C_6$ aryl; aralkyl and alkaryl wherein the alkyl and aryl portions thereof are as described immediately above; ether groups or ester groups wherein said ether and ester groups are as described in conjunction with $R_5$ of structural formula (IIIa) above, said $R_{11}$ substituents preferably being inert under reaction conditions. In addition, any two $R_{11}$ groups located on adjacent carbons of said $Z_2$ to $Z_5$ groups of structural formula (XIIa) together can constitute part of a monocyclic, or fused bicyclic ring system, which partial ring system is: (a) aromatic, or heteroaromatic in nature, said heteroatom being nitrogen and (b) completed by, and fused with, parent structure (XIIa) above, through said adjacent carbons of the $Z_2$ to $Z_5$ groups. Moreover, the replaceable hydrogens of the multicyclic ring system incorporating any two of said $R_{11}$ groups together, can be substituted with hydroxy, alkyl, aryl, aralkyl, and alkaryl groups as defined above.

In structural formula (XIIb), $Z_7$ to $Z_9$ independently represent a methylidyne group (—CH=), or a substituted methylidyne group (=CR'$_{11}$) wherein R'$_{11}$ is independently selected from the group consisting of alkyl, aryl, aralkyl, and alkaryl as described in conjunction with $R_{11}$. The substituent $R_{12}$ of formula (XIIb) is selected from the group consisting of alkyl, aryl, aralkyl, and alkaryl as described in conjunction with $R_{11}$ of formula (XIIa), preferably $C_1$ to $C_5$ alkyl.

Furthermore as discussed above, in order to impart a rate promoting effect to the co-catalysts II described by formula (XIIa), said formula is also functionally limited by the priviso that in any cyclic ring system defined thereby which contains more than one tertiary nitrogen, the relative configuration between any of said nitrogens within said cyclic ring system: (i) excludes a 1,3- and 1,4-positional relationship; and (ii) prevents co-catalyst II from acting, under reaction conditions, as a bidentate ligand in conjunction with co-catalyst I.

Preferably at least one, most preferably both, of said $Z_2$ and $Z_6$ groups of formula (XIIa) are methylidyne.

Likewise, preferably at least one, most preferably both, of said $Z_7$ and $Z_8$ groups of formula (XIIb) are methylidyne.

Representative compounds suitable for use as co-catalysts II(b) and (c) are provided at Table A herein. The most preferred co-catalyst II is pyridine.

TABLE A

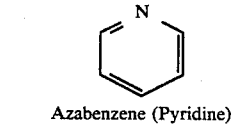

Azabenzene (Pyridine)

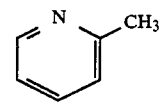

2-methyl-1-azabenzene

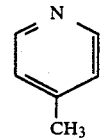

4-methyl-1-azabenzene
(4-methylpyridine)

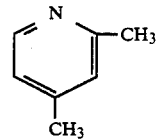

2,4-dimethyl-1-azabenzene

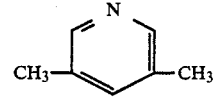

3,5-dimethyl-1-azabenzene
(3,5-dimethylpyridine)

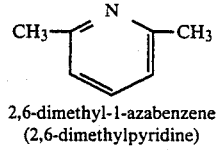

2,6-dimethyl-1-azabenzene
(2,6-dimethylpyridine)

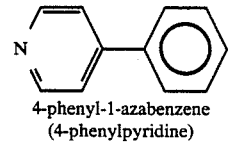

4-phenyl-1-azabenzene
(4-phenylpyridine)

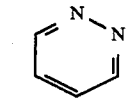

1,2-diazabenzene
(Pyridazine)

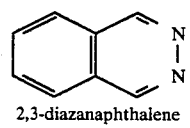

2,3-diazanaphthalene
(Phthalazine)

TABLE A-continued

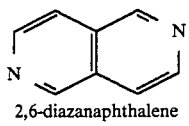
2,6-diazanaphthalene

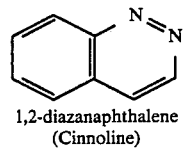
1,2-diazanaphthalene
(Cinnoline)

2-azanaphthalene
(Isoquinoline)

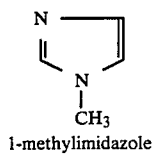
1-methylimidazole

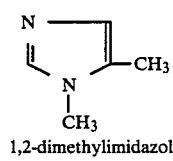
1,2-dimethylimidazole

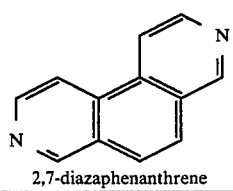
2,7-diazaphenanthrene

The amount of co-catalyst II employed in the reaction system will affect the performance thereof. Such amount is selected to not only achieve an increase in the overall rate of cyclic carbonate ester production but also increase the rate of the vicinal diol intermediate relative to its absence. It has been found that more co-catalyst II is desired for the overall two step reaction, than would otherwise be indicated when performing only an olefin hydroxylation reaction by itself.

Accordingly, it is contemplated that effective amounts of co-catalyst II will generally constitute a ratio of moles of co-catalyst II per mole of the copper metal employed as co-catalyst I of typically from about 0.25 to about 3, preferably from about 0.5 to about 2, and most preferably from about 0.75 to about 1.5 (e.g. 1).

If too much co-catalyst II is employed (e.g. solvent amounts) in the reaction mixture, no effect on reaction rate is observed relative to its absence. Thus, it is not contemplated to employ co-catalyst II as solvent for the reaction system, if one seeks a rate promoting effect attributable thereto.

Accordingly, the reaction mixture will comprise typically less than 50%, preferably less than 15%, and most preferably less than 5%, by weight of co-catalyst II, based on the total weight of the liquid contents of the reaction mixture.

(C) Co-catalyst III

Co-catalyst III is a term used herein to describe at least one halo-containing material, typically employed in an organic or inorganic salt form, which functions in conjunction with co-catalysts I and II to further improve the rate and/or selectivity of the overall reaction. The use of co-catalyst III is optional although preferred.

Suitable promoters of co-catalysts III include alkali metal (e.g., Li, Na, K, Rb, Cs, and Fr), and alkaline earth metal (e.g., Be, Mg, Ca, Sr, Ba, and Ra): halides, tetra hydrocarbyl (e.g. $C_1$ to $C_5$ alkyl) ammonium halides, tetra hydrocarbyl (e.g. $C_1$ to $C_5$ alkyl) phosphonium halides, hydrogen halides; halogenated hydrocarbons wherein the hydrocarbyl portion thereof is selected from alkyl (e.g. $C_1$ to $C_5$ alkyl); aryl, (e.g. $C_6$ to $C_{10}$ aryl), aralkyl, alkaryl and cycloalkyl (e.g. $C_4$ to $C_{10}$ cycloalkyl); Group III-b (i.e., B, AL, Ga, In, Tl), IV-b (i.e., Si, Ge, Sn, Pb), V-b (i.e., N, P, As, Sb, Bi) and VI-b (i.e., S, Se, Te, Po) halides.

Accordingly, while any effective amount of co-catalyst III can be employed to increase the reaction rate, it is contemplated that such effective amounts constitute typically from about 0.1 to about 10,000 mole percent, preferably from about 10 to about 1000 mole percent, and most preferably from about 25 to about 75 mole percent, co-catalyst III, based on the total number of moles of osmium in the osmium catalyst employed.

Illustrative examples of suitable co-catalyst combinations include $CuBr_2$ and DABCO; $Cu(NO_3)_2$, HMTA and NaBr; $CuCl_2$, DABCO, and NaBr; $CuBr_2$, HMTA, and NaBr; copper acetate, DABCO, and tetraethyl ammonium chloride; $CuI_2$, HMTA, and KBr; $Cu(NO_3)_2$, DABCO, and CuBr; CuI, HMTA, and NaBr; and $Cu(NO_3)_2$, DABCO, and n-butyl bromide; $CuBr_2$ and pyridine; $Cu(NO_3)_2$, pyridine and NaBr; $CuCl_2$, pyridine, and NaBr; $CuBr_2$ pyridine, NaBr; copper acetate, pyridine, and tetraethyl ammonium chloride; $CuI_2$, pyridine, and KBr; and $Cu(NO_3)_2$, pyridine, and n-butyl bromide.

The decision of whether to employ a co-catalyst III is affected by the observation that the presence of a halo-moiety in the reaction mixture has beneficial effects on the rate and/or selectivity of the reaction. More specifically, by "halo-" is meant to include halogen in the form of organic and inorganic halide salts or complexes, halogenated hydrocarbons, and hydrogen halides. Accordingly, it is preferred to provide a halo-source in the reaction mixture. This is typically achieved through the use of a copper halide as co-catalyst I. If, however, co-catalyst I is not employed as a halide salt, it is preferred to introduce a halo-source through an alternative means. This can be easily achieved through appropriate use of co-catalyst III.

Thus, for optimum performance of the reaction system, it is preferred to establish a balance, in terms of amounts, between osmium in the osmium catalyst, the copper of co-catalyst I, and halogen in the halo-source present in the reaction mixture. Accordingly, it is contemplated that the mole ratio of Os:copper:halogen in the halo-source, in contact with the olefin to be converted be controlled to be typically from about 1:1:1 to about 1:100:1000, preferably from about 1:1:25 to about 1:80:500, and most preferably from about 1:1:20 to about 1:50:50.

While the olefin conversion reaction can be conducted in a heterogeneous multiphase system, the preferred mode for conducting the same is in a liquid reaction mixture, preferably provided as a homogeneous or substantially homogeneous medium, preferably by using an inert organic solvent to dissolve, where possible, whatever components are employed in the catalyst and co-catalyst system and reactants. Partial immiscibility of the solvent with water is acceptable although not preferred. By an inert solvent is meant one which does not undergo oxidation during the course of the reaction.

Suitable inert organic solvents include aliphatic or aromatic alcohols having from 1 to about 10 carbon atoms, preferably tertiary alcohols, aliphatic or aromatic ketones having from 3 to about 10 carbon atoms, aliphatic or alicyclic ethers having from 2 to about 10 carbon atoms, N,N-dialkyl amides having from 3 to about 10 carbon atoms, nitriles having from about 2 to about 10 carbons, aliphatic or aromatic sulfoxides having from 2 to about 14 carbon atoms, aliphatic or aromatic sulfones having from 2 to about 14 carbon atoms, and the like. Examples of suitable solvents include methanol, ethanol, propanol, butanol, hexanol, decanol, t-butyl alcohol, t-amyl alcohol, benzyl alcohol, acetone, methylethyl ketone, methylbutyl ketone, acetophenone, ethylene glycol, propylene glycol, diethylene glycol, tetraethylene glycol, dimenthyl formamide, diethyl formamide, dimethyl acetamide, dimethyl sulfoxide, diethyl sulfoxide, N,N-butyl sulfoxide, diphenyl sulfoxide, dibenzyl sulfoxide, dimethyl sulfone, diethyl sulfone, tetramethylene sulfone (sulfolane), diphenyl sulfone, acetonitrile, dioxane, tetrahydrofuran, tetrahydropyran, dioxalane, adiponitrile, N-methylpyrrolidone, and mixtures thereof.

The preferred solvents include those which are substantially or completely miscible with water such as t-butyl alcohol, methanol, as well as glycols and/or polyols derived from the olefin being hydroxylated.

The most preferred solvents are dipolar and aprotic such as sulfolane, acetonitrile, N,N-dimethylacetamide, N,N-dimethylformamide, N-methylpyrrolidone, adiponitrile, and dimethyl sulfone.

The inert solvent is preferably employed in amounts sufficient to achieve a homogeneous solution with respect to at least the olefin, catalyst and co-catalyst system. Typically such amounts can vary from about 0 to about 98% (e.g. 10 to 90%), preferably from about 10 to about 90%, and most preferably from about 20 to about 80%, by weight, based on the total weight of the reaction mixture.

The amount of water provided to, and/or present in the reaction mixture is critical to the present invention. If too much water is present, it will supress the cyclic carbonate ester formation. However, if not enough water is present, the olefin will not be converted and neither the vicinal diol intermediate nor the cyclic carbonate ester believed to be derived therefrom will produced. Moreover, the amount of water employed is also directly related to the ratio of co-catalysts II/I.

Since each mole of cyclic carbonate ester formed produces a mole of water as a co-product, in the same reaction mixture containing the olefin, it has been found possible to use the water co-product thereby produced as a source of water for olefin conversion. However, it has further been found that the water co-produced with the cyclic carbonate ester generally will not desirably constitute the sole source of water in the reaction mixture. This stems from the fact that the olefin conversion reaction consuming water occurs at a faster rate than the cyclic carbonate ester and water formation, and further by the fact that the presence of a certain residual amount of water, which is not consumed, has been found to be desirable, as a result of the overall kinetics of reaction, to achieve an acceptable overall reaction rate.

Accordingly, the amount of water in the reaction mixture is controlled broadly to achieve a mole ratio of water to molar amount of ethlenic unsaturation in the olefin to be converted of from about 0.1:1 to about 20:1, preferably from about 0.25:1 to about 10:1, and most preferably from about 0.50:1 to about 5:1. Subject to the above molar constraints the amount of water in the reaction mixture typically will vary from about 0.5 to about 90%, preferably from about 1 to about 30%, and most preferably from about 2 to about 15%, by weight, based on the total weight of the reaction mixture. Preferably the amount of water employed is less than that which will cause separation of the reaction mixture into an aqueous phase and organic phase.

Furthermore, when the moles of co-catalyst II per mole of Cu in co-catalyst I varies as indicated above, the ratio of the moles of water per mole of Cu in said co-catalyst I will typically vary from about 5 to about 60, preferably from about 10 to about 40, and most preferably from about 10 to 20.

The amount of water employed within the aforedescribed ranges is also influenced by the amount of $O_2$ in the system. Thus, the mole ratio of $H_2O$ to $O_2$ dissolved in the reaction mixture is typically controlled to be from about 1:1 to about 20:1, preferably from about 1:1 to about 15:1, and most preferably from about 1:1 to about 5:1.

When the appropriate amount of water is present, it will typically be consumed at a rate faster than it is produced. Consequently, make-up water is typically added based on an analysis of the reaction mixture and/or the water partial pressure of the reaction mixture. Additional water can also be supplied by introducing a glycol of the feed olefin into the feed to increase the in-situ formation of water.

The primary oxidant employed in the present invention is molecular oxygen. Such oxygen can be added as pure oxygen or as part of an oxygen containing gas such as air, or some other oxygen containing gas having one or more inert gases such as $N_2$ present therein. Generally, the oxygen containing gas is present within, preferably dissolved in, the reaction mixture in amounts sufficient to achieve conversion of the olefin and formation of the cyclic carbonate ester.

Accordingly, the molar ratio of oxygen to olefin ethylenic unsaturation can vary widely but for safety reasons it is preferably maintained outside explosive limits.

For example, when converting ethylene or propylene, if oxygen is in excess of stoichiometry, the ratio typically will be 98 weight % oxygen or more and 2% or less of the olefin. Preferably, however, the olefin is employed in excess, preferably large excess, of stoichiometry, and the oxygen concentration of the oxidizing gas typically will be about 10 mole % oxygen and about 90 mole % olefin. When oxygen is in excess of stoichiometry, olefin can be added as the reaction proceeds. On the other hand, where the olefin is in excess of stoichiometry, oxygen can be added during the reaction as the oxygen is consumed.

Accordingly, and in view of the above, the oxygen containing gas preferably is dissolved in the reaction mixture in an amount sufficient to achieve a molar ratio of ethylenic unsaturation in the olefin to be converted to oxygen of from about 1:1 to about 100:1, preferably from about 1:1 to about 20:1, and most preferably outside the explosive limits of the reaction mixture. It is to be noted, that when either olefin or $O_2$ is employed in substantial excess of stoichiometry for safety reasons the conversion in a batch process will necessarily be very low if based on the component present in large excess. This is not a problem in a continuous process since unreacted components are recycled.

The amount of carbon monoxide present in the reaction mixture is not critical and can vary over wide limits. Thus, the molar ratio of olefin ethylenic unsaturation to be converted to CO is typically controlled to be from about 1:0.5 to about 20:1, preferably from about 1:0.5 to about 10:1, and most preferably from about 1:0.5 to about 3:1.

The pH of the reaction mixture during reaction need not be rigidly controlled although it will preferably not be allowed to drop below about 4, preferably not below about 6. Likewise, the pH of the reaction mixture preferably will not be allowed to exceed about 12 although the process can still be conducted at a pH below 4 and above about 12. Active pH control is generally not needed since the pH of the reaction mixture will typically autogeneously vary between about 4 and 12, preferably between about 5 and 12, and most preferably between about 5 and 8.

The conversion reaction is typically conducted at temperatures of from about 40° to about 250° C., preferably from about 60° to about 200° C., and most preferably from about 80° to about 170° C.

Furthermore, since it is preferred to conduct the reaction in the liquid phase, the reaction temperature is typically selected in conjunction with the reaction pressure to achieve this goal.

For the production of cyclic carbonate esters derived from any unsaturated gaseous olefin, the latter may be bubbled through the reaction mixture containing the components described herein or it may be introduced under pressure. Likewise with the oxygen containing gas and CO. However, it is preferred that the reaction take place in the liquid phase. Consequently, sufficient pressure is preferably employed to maintain the reactants (i.e., water, olefin, oxygen, and CO) in the liquid phase and/or to dissolve the reactants into the liquid reaction mixture.

Although the magnitude of the pressure is not critical, it determines the amount of the reactants that are present in the reaction mixture and therefore affects the rate of reaction. Accordingly, the total reaction pressure of the reaction mixture is typically controlled to be from about 200 to about 4000 psig, preferably from about 300 to about 1600 psig, and most preferably from about 350 to about 1000 psig at the aforenoted reaction temperatures. The partial pressure of each reactant, i.e., water, olefin, oxygen, and CO, can be controlled to achieve the aforenoted molar ratios.

Accordingly, the partial pressure of the reactant olefin (at reaction temperature) thereof is typically controlled to be from about 200 to about 3000, preferably from about 250 to about 2000, and most preferably from about 300 to about 1500 psig.

The partial pressure of oxygen (at reaction temperature) employed typically will vary from about 10 to about 2000, preferably from about 15 to about 500, and most preferably from about 20 to about 200 psig.

The partial pressure of carbon monoxide (at reaction temperature) will typically vary from about 50 to about 4000, preferably from about 75 to about 2000, and most preferably from about 100 to about 1000 psig.

In carrying out the invention, olefin, water, oxygen, CO, osmium catalyst, co-catalysts, and optional inert solvent are brought into contact in a manner and under conditions sufficient to convert the olefin, to its corresponding cyclic carbonate ester in the liquid phase.

Accordingly, the reaction can be performed as a batch reaction, preferably as a continuous reaction, or as a semi-continuous reaction. In the batch reaction, the osmium catalyst is charged into the reaction vessel as a solution in the inert solvent along with the co-catalyst I, co-catalyst II, optional co-catalyst III, water, and olefin if in liquid form. The reaction vessel is then pressurized with oxygen, CO, and olefin if in gaseous form. It may be desirable to heat the liquid reaction mixture to reaction temperature prior to pressurizing with the reactant gases. The reaction is allowed to proceed to the desired degree of completion.

In the continuous process, the reaction mixture components can be introduced into the inlet of an elongated reactor at a rate such that substantially complete reaction will have taken place by the time the reaction mixture reaches the reactor outlet. The reaction can be carried out in a semi-continuous manner by metering the reactant mixture components into a series of two or more tank reactors at the appropriate rate to maintain the reactor liquid level.

Additionally, the process may be run in either of the aforementioned modes by altering the reaction conditions, and/or, the reactant, solvent, catalyst, and co-catalysts concentrations during the course of the reaction. Thus, the process may be run by changing the temperature, pressure, catalyst concentration, and/or reactant concentration.

The spent reaction mixture after removal of unreacted olefin is a solution of cyclic carbonate ester, glycol, by-products, if any, solvent, water, and catalyst system components. The volatile components are distilled out of the reaction mixture into various fractions leaving non-volatile catalyst system components in the still. The product carbonate ester is then separated from the high boiling distillate and the remainder returned to the reactor containing recycled catalyst components.

The following examples are given as specific illustrations of the claimed invention. It should be understood, however, that the invention is not limited to the specific details set forth in the examples. All parts and percentages in the examples as well as in the remainder of the specification are by weight unless otherwise specified.

Unless otherwise specified, in the following examples, selectivity, yield, and conversion are calculated as follows:

$$\% \text{ Selectivity} = \frac{\text{moles of Carbonate (or glycol) formed}}{\text{moles of Oxygenated Products Produced}} \times 100$$

$$\% \text{ Conversion} = \frac{\text{moles of Oxygenated Products}}{\text{moles of Olefin Charged}} \times 100$$

$$\% \text{ Yield} = \frac{(\% \text{ Conversion}) (\% \text{ Selectivity})}{100}$$

EXAMPLE 1

A series of runs were conducted using propylene as the olefin. This series of runs is intended to illustrate the effect of water content on cyclic carbonate formation. The general procedure employed was as follows. Two solutions were prepared as follows: $OsO_4$ (0.18 mmole, 1.74 g of 2.5 wt. % TBA solution) and pyridine (25 mmole) were mixed in sulfolane (15 ml) to form solution 1. $CuBr_2$ (5 mmole) was dissolved in $H_2O$ (300 mmole) and sulfolane (40 ml) was added to form solution 2. Solution 1 was charged to a stirred 300 cc autoclave followed by solution 2 with stirring. Propylene (15 g) was then charged to the reactor. The stirred solution was then heated to 130° C. and carbon monoxide (400 psig, 226 mmole) was added. To this solution molecular oxygen (50 mmole) was charged. (The oxygen pressure reported at Table 1 reflects the pressure drop from an oxygen bomb at ambient temperature (i.e. 25° C.) when the oxygen from the bomb is introduced into the reactor.) A total pressure of 910 psig was recorded in the reactor. The reaction was allowed to proceed for 30 minutes after the addition of molecular oxygen. The mixture was then quickly cooled and degassed. A green homogeneous solution was removed from the autoclave and analyzed by gas chromatography. Propylene glycol (76.0 mmole, 90% selectivity) and propylene carbonate (8.0 mmole, 10% selectivity) were found. The results are summarized at Table 1, Run 1.

Runs 2 to 4 were conducted following the above procedure generally but varying various reaction mixture components as reported at Table 1. The results of product anlaysis as well as the process variables employed are reported at Table 1, Runs 2 to 4. In contrast to Run 1, however, CO was also charged at 25° C. before bringing the reactor contents to reaction temperature for Runs 2 to 4. Moreover, for Run 4, oxygen was added in increments from a 300 cc addition vessel at intervals of about 30 minutes during the course of the reaction until the amount of $O_2$ specified at Table 1 was achieved. Consequently, the reaction time reported for Run 4 was measured from the initiation of said $O_2$ addition.

EXAMPLE 2

A further series of runs was conducted generally in accordance with Example 1, Run 2 to illustrate the effect of water, in conjunction with the $CuBr_2$/pyridine ratio. The process variables as well as the results of product analysis are summarized at Table 1, Runs 5 to 11.

EXAMPLE 3

This example illustrates the effect of including propylene glycol in the feed in the absence of water in the initial reaction mixture and in the initial presence of 200 mmoles of water.

Accordingly, two runs were conducted in accordance with the procedure of Example 1. The amounts and identity of reaction mixture components as well as reaction conditions are summarized at Table 1, Runs 12 and 13. In addition to the CO, $O_2$ and propylene specified, 100 mmoles of propylene glycol were also introduced in the initial reaction mixture. The results of product analysis are provided at Table 1, Runs 12 and 13. Note that oxygen addition was conducted for these Runs 12 and 13 in accordance with Run 4, while CO addition was conducted in accordance with Run 1.

TABLE 1

| Run No. | CO (psig)(mm) | $O_2$ (psig)(mm) | $C_3=$ (psig)(mm) | Sulfolane ml | $OsO_4$ (mm) | $CuBr_2$ (mm) | Py (mm) | $H_2O$ (mm) |
|---|---|---|---|---|---|---|---|---|
| 1 | 400/226 | 60/50 | 444/357 | 73 | 0.20 | 5 | 25 | 200 |
| 2 | 400/226 | 110/92 | 470/357 | 71 | 0.20 | 5 | 25 | 300 |
| 3 | 600/253 | 60/50 | 228/119 | 45 | 0.20 | 5 | 10 | 100 |
| 4 | 600/260 | 60/50 | 180/124 | 61 | 0.20 | 5 | 13 | 1070 |
| 5 | 600/260 | 60/50 | 560/357 | 71 | 0.20 | 5 | 10 | 300 |
| 6 | 600/260 | 60/50 | 540/357 | 76 | 0.20 | 10 | 10 | 100 |
| 7 | 400/226 | 60/50 | 450/239 | 44 | 0.20 | 10 | 10 | 200 |
| 8 | 600/260 | 60/50 | 540/357 | 70 | 0.20 | 10 | 10 | 500 |
| 9 | 500/278 | 120/100 | 540/357 | 76 | 0.20 | 10 | 5 | 100 |
| 10 | 500/264 | 120/100 | 540/357 | 73 | 0.20 | 10 | 5 | 100 |
| 11 | 500/278 | 120/100 | 540/357 | 74 | 0.20 | 10 | 5 | 200 |
| **12 | 500/278 | 180/150 | 540/357 | 38 | 0.20 | 10 | 10 | 0 |
| **13 | 500/278 | 120/100 | 540/357 | 64 | 0.20 | 10 | 10 | 200 |

| Run No. | Reaction Conditions | | | Sel(%) | | | Molar Ratio |
|---|---|---|---|---|---|---|---|
|  | Temp. (°C.) | Time* (hrs) | Conv. (%) | PG | PC | PC Yield (%) | PG/PC |
| 1 | 130 | 1 | 13 | 90 | 10 | 1.0 | 11 |
| 2 | 130 | 1 | 13 | 91 | 9 | 1.2 | 10 |
| 3 | 120 | 2 | 10 | 72 | 18 | 1.8 | 4.7 |
| 4 | 110 | 4 | 58 | 96 | 3 | 1.7 | 32 |
| 5 | 140 | 3 | 22 | 59 | 24 | 5.3 | 2.5 |
| 6 | 120 | 5 | 12 | 52 | 30 | 3.6 | 1.8 |
| 7 | 120 | 4 | 18 | 63 | 33 | 5.9 | 1.9 |
| 8 | 120 | 3 | 17 | 83 | 5 | .85 | 17 |
| 9 | 120 | 3 | 9 | 50 | 33 | 3.0 | 1.4 |
| 10 | 140 | 3 | 13 | 46 | 27 | 3.5 | 1.7 |
| 11 | 120 | 3 | 13 | 62 | 17 | 2.2 | 3.5 |
| **12 | 120 | 4 | 7 | 32 | 52 | 3.6 | 1.6 |

TABLE 1-continued

| **13 | 120 | 2 | 4 | 29 | 53 | 2.1 | 1.8 | mm = millimoles  
C₃ = propylene  
PG = propylene glycol  
PC = propylene Carbonate  
Py = Pyridine  
*Time measured from completion of oxygen addition except for Run 4.  
**100 mmoles of PG in feed

Discussion of Results of Runs 1 to 13

Referring to Runs 1 and 2, it can be seen that at a 1 to 5 ratio of CuBr$_2$:pyridine a selectivity of only 8 to 9% to cyclic carbonate ester is achieved using 200 and 300 mmoles of water respectively. However, when the CuBr$_2$:pyridine ratio is reduced to 1:2 and the initial water content reduced to 100 mmoles (Run 3) the selectivity to propylene carbonate is increased to 18%. In contrast, with the use of 1070 mmoles of water at about the same 1:2 ratio of co-catalysts, the selectivity to propylene carbonate drops to only 3%. The high propylene glycol selectivity of 96% illustrates that reaction conditions most suitable for glycol formation are not suitable for carbonate ester formation.

Referring to Run 5 it can be seen that with a 1:2 ratio of CuBr$_2$:pyridine and 300 mmoles of H$_2$O, the carbonate selectivity is increased to 24%.

It is concluded from Runs 1 to 5 that the CuBr$_2$:pyridine ratio preferably should not exceed about 1:2 and when operating at this ratio the Cu:H$_2$O molar ratio preferably should not exceed about 1:60.

Referring to Runs 6 to 8 which employ a 1:1 CuBr$_2$:pyridine mole ratio it can be seen that 500 mmoles of H$_2$O (i.e. Cu:H$_2$O of 1:50) drastically reduces the carbonate selectivity to 5%. At this ratio of co-catalysts it is preferred to operate at a Cu:H$_2$O mole ratio between about 1:10 to about 1:20. Furthermore, comparing Run 6 with Run 3 it can be seen that at an initial equal water content of 100 mmoles, a 1:1 mole ratio of co-catalyst results in nearly a doubling of selectivities from 18 to 30%. Thus, a 1:1 ratio of co-catalysts I:II is preferred over a 1:2 ratio.

Referring to Runs 9 to 11, it can be seen that at a 2:1 mole ratio of co-catalysts I:II, the ratio of Cu:H$_2$O of 1:10 achieves almost one and a half times the selectivity of a rate of 1:20. Thus, in the regime of a co-catalyst I:II ratio of 2:1, the carbonate selectivity is more sensitive to increasing water content than a 1:1 ratio of co-catalysts, and much more sensitive to increasing water content than when operating at a co-catalyst I:II ratio of 1:2.

Generalizing from the above data, it is concluded that the co-catalyst I:II ratio can vary from 2:1 to about 1:2 at a co-catalyst I:water ratio of from about 1:10 to about 1:60 and the particular combination of such ratios will be influenced by the selection of the co-catalyst I:II ratio selected.

Referring to Run 12, it can be seen that when propylene glycol is added to the feed in the absence of water, extremely high selectivities to carbonate are obtained. It has been calculated that 76 mmoles of water were produced by propylene carbonate formation, and of this amount 27 mmoles of water were reacted. Thus, it is concluded that a glycol feed can be used to control water content. Run 13 illustrates that the inclusion of water in addition to glycol in the feed results in little change in overall yield, although the rate of conversion is slightly enhanced.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for preparing at least one cyclic alkylene carbonate ester which comprises reacting in a liquid phase admixture at least one olefin containing at least one ethylenic unsaturation, water, molecular oxygen, and carbon monoxide in the presence of an osmium containing catalyst composition, thereby forming said cyclic alkylene carbonate ester product, with the proviso that the total amount of water present in said liquid phase during reaction being a molar ratio of water to ethylenic unsaturation to be reacted of from about 0.1:1 to about 20:1; said catalyst composition comprising:

(A) at least one catalytically active osmium containing compound;

(B) an amount of at least one copper containing compound co-catalyst I effective to increase at least one of the rate and selectivity in the formation of said cyclic carbonate ester product relative to its absence;

(C) at least one co-catalyst II in an amount effective to increase the rate of said cyclic carbonate ester product formation relative to its absence, said co-catalyst II being selected from at least one member of the group consisting of:

(i) 1,4-diazabicyclo (2.2.2) octane;
(ii) hexamethylenetetraamine; and
(iii) at least one compound represented by at least one of the structural formulae:

(XIIa)

or

(XIIb)

wherein:
(1) in structural formula (XIIa):
(a) $Z_2$ to $Z_6$ independently represent a member selected from the group consisting of a methylidyne group, a substituted methylidyne group represented, by the formula $=CR_{11}$, and a tertiary nitrogen group; said $R_{11}$ substituent being selected from the group consisting of hydroxy, alkyl, aryl, aralkyl and alkaryl; and (b) any two of said $R_{11}$ substituents located on adjacent carbons of said $Z_2$ to $Z_5$ groups of structural formula (XIIa) together can constitute part of a monocyclic or fused bicyclic ring system, which partial ring systems are (i) aromatic, or heteroaromatic in nature, said heteroatom being nitrogen, and (ii) completed by, and fused with parent structure (XIIa) through said adjacent carbons of $Z_2$ to $Z_5$ groups; and (2) in structural formula (XIIb):

(a) $Z_7$ to $Z_9$ independently represent a member selected from the group consisting of a methylidyne group, and a substituted methylidyne group represented by the formula $\equiv CR'_{11}$ wherein $R'_{11}$ is independently selected from the group consisting of alkyl, aryl, aralkyl, and alkaryl; and (b) $R_{12}$ is selected from the group consisting of alkyl, aryl, aralkyl, and alkaryl.

2. The process of claim 1 wherein the osmium containing compound is selected from the group consisting of osmium oxide, osmium-halide, osmium carbonyl, ionic osmium oxide, and mixtures thereof; co-catalyst I comprises a copper salt having an anion, wherein said anion is of a member independently selected from the group consisting of halide, carboxylate, aryloate, aryolate, pseudo halide, $R_{10}S^-$, $HS^-$, $R_{10}Se^-$, $HTe^-$ and $R_{10}Te^-$, $R_{10}$ being alkyl of from about 1 to about 10 carbons.

3. The process of claim 2 wherein said catalyst composition additionally comprises at least one halo-source in an amount effective to increase at least one of the rate and selectivity of the reaction relative to its absence.

4. The process of claim 3 wherein said halo-source is at least one halide salt wherein the cation of said salt is of a member independently selected from the group consisting of alkali metal, alkaline earth metal, tetrahydrocarbyl ammonium, and tetrahydrocarbyl phosphonium.

5. The process of claim 1 wherein the olefinic compound is an alpha olefin which contains from about 2 to about 20 carbons.

6. The process of claim 1 wherein said co-catalyst I is a copper halide salt.

7. The process of claim 1 wherein co-catalyst II is selected from the group consisting of pyridine, methylpyridine, dimethylpyridine, 4-phenylpyridine, 1,2-diazabenzene, methylimidazole, dimethylimidazole, 1,4-diazabicyclo[2.2.2]octane, hexamethylenetetramine, and mixtures thereof.

8. The process of any one of claims 3, 4, 6, and 7 wherein the osmium in the osmium compound, co-catalyst I, and halo source, in said catalyst composition, are present in said composition in a molar ratio of osmium:copper of co-catalyst I:halogen in the halogen source of from about 1:1:1 to about 1:100:1000.

9. The process of claim 7 wherein said co-catalyst II is selected from the group consisting of pyridine, 3,5-dimethylpyridine, 2,4-dimethylpyridine, 2-methylpyridine, 4-methylpyridine, 4-phenylpyridine, 1-methylimidazole, 1,2-dimethylimidazole, and mixtures thereof.

10. The process of claim 1 wherein said liquid reaction mixture is homogeneous, and wherein in said liquid reaction mixture: the osmium compound is present in an amount sufficient to achieve a ratio of moles of osmium in the osmium compound to moles of ethylenic unsaturation to be reacted of from about $1 \times 10^{-2}:1$ to about $1 \times 10^{-6}:1$; co-catalyst I is present in an amount sufficient to achieve a ratio of moles of osmium in the osmium compound to moles of copper in co-catalyst I of from about 1:1 to about 1:500; and co-catalyst II is present in an amount sufficient to achieve a ratio of the moles thereof per mole of copper in the co-catalyst I of from about 0.5 to about 2; water is present in an amount sufficient to achieve a mole ratio of water per mole of copper in co-catalyst I of from about 10 to about 60; inert inorganic solvent is present in an amount of from about 20 to about 80%, by weight, based on the weight said reaction mixture; oxygen is present in an amount sufficient to achieve a molar ratio of ethylenic unsaturation in the olefin to be converted to oxygen of from about 1:1 to about 20:1; and carbon monoxide is present in an amount sufficient to achieve a molar ratio of ethylenic unsaturation to be converted to cyclic carbonate of from about 1:0.5 to about 10:1.

11. The process of claim 10 wherein the inert organic solvent is selected from the group consisting of sulfolane, acetonitrile, N,N-dimethylacetamide, N,N-dimethylformamide, and mixtures thereof.

12. The process of claim 11 wherein co-catalyst I is $CuBr_2$; co-catalyst II is pyridine, and the osmium compound is selected from the group consisting of $OsO_4$, $OsBr_3$ and mixtures thereof.

13. The process of claim 10 wherein the reaction temperature is from about 60° to about 200° C., and the reaction pressure is from about 300 to about 1600 psig.

14. The process of claim 1 wherein olefin, oxygen and carbon monoxide are continuously introduced into the reaction mixture and the cyclic alkylene carbonate ester product is continuously removed the reaction mixture comprising (a) a molar ratio of water to ethylenic unsaturation to be reacted between about 0.5:1 and about 5:1, and (b) a ratio of moles of water per mole of copper in co-catalyst I of from about 109 to about 20.

15. The process of claim 14 wherein a vicinal diol is also introduced into the reaction mixture as a means for controlling the water content of the reaction mixture.

16. The process of claim 14 wherein the ratio of moles of co-catalyst II per mole of copper in co-catalyst I in the reaction mixture is from about 0.75 to about 1.5.

17. The process of claim 16 wherein said co-catalyst II/I ratio is about 1.

* * * * *